United States Patent [19]

Wells

[11] Patent Number: 5,001,102
[45] Date of Patent: Mar. 19, 1991

[54] HETEROGENEOUS CATALYSTS

[75] Inventor: James E. Wells, Ardmore, Pa.

[73] Assignee: PQ Corporation, Valley Forge, Pa.

[21] Appl. No.: 295,681

[22] Filed: Jan. 11, 1989

[51] Int. Cl.⁵ .................. B01J 27/18; B01J 27/185; B01J 27/188
[52] U.S. Cl. .................. 502/213; 423/311; 502/208; 502/210; 560/205; 560/224
[58] Field of Search ............ 502/208, 210, 213; 423/311; 560/205, 224

[56] References Cited

U.S. PATENT DOCUMENTS

| | | | |
|---|---|---|---|
| 1,882,712 | 10/1932 | Andrussow et al. | 502/213 |
| 3,264,347 | 8/1966 | Sennewald et al. | 560/205 |
| 3,442,935 | 5/1969 | Pine et al. | 560/205 |
| 3,644,497 | 2/1972 | Mesich | 560/205 |
| 4,143,082 | 3/1979 | Bartek et al. | 502/210 |
| 4,324,908 | 4/1982 | Grasselli et al. | 502/208 |
| 4,364,856 | 12/1982 | Teng et al. | 502/210 |
| 4,410,727 | 10/1983 | Ruszala | 502/213 |
| 4,410,728 | 10/1983 | Daniel | 502/213 |
| 4,427,792 | 1/1984 | Pedersen et al. | 502/213 |
| 4,507,495 | 3/1985 | Dougherty et al. | 560/205 |
| 4,563,439 | 1/1986 | Bremer et al. | 502/210 |
| 4,619,907 | 10/1986 | Johnson et al. | 502/210 |
| 4,742,035 | 5/1988 | Pederson et al. | 502/210 |
| 4,748,269 | 5/1988 | Meixner et al. | 560/205 |

FOREIGN PATENT DOCUMENTS

| | | | |
|---|---|---|---|
| 22302 | 2/1979 | Japan | 502/210 |
| 2107305 | 4/1983 | United Kingdom | 560/205 |

Primary Examiner—Wayne A. Langel
Attorney, Agent, or Firm—Ernest G. Posner

[57] ABSTRACT

Non-stoichiometric, heterogeneous, amorphous catalysts for preparing esters of acrylic and methacrylic acids.

1 Claim, No Drawings

HETEROGENEOUS CATALYSTS

BACKGROUND OF THE INVENTION

This invention relates to heterogeneous metal catalysts. In particular, this invention relates to the catalysts, methods of preparing them, and their use in the production of unsaturated hydroxyalkyl esters.

The catalyst art has long recognized the utility of certain phosphate and metal phosphate catalyst compositions. Among such materials are aluminum phosphates, both stoichiometric AlPO$_4$ and non-stoichiometric Al(PO$_4$)$_x$ where x is less than 1. For instance, U.S. Pat. No. 3,904,550 describes the preparation of such materials and their use as desulfurization catalysts. U.S. Pat. No. 3,801,704 teaches that aluminum phosphates can be used for catalytic dehydration. U.S. Pat. No. 4,524,225 demonstrates that such phosphates also function as hydrogenation catalysts. Other cited uses of aluminum phosphates include cracking (U.S. Pat. No. 4,382,878), ether rearrangement (U.S. Pat. No. 4,538,008), and polyolefin synthesis (U.S. Pat. Nos. 4,364,839; 4,547,479; 4,424,139; 4,397,765; 4,596,862; 4,504,638; and 4,364,854). In all of these cases stoichiometric or non-stoichiometric aluminum phosphates are taught and methods for making them described.

Among other phosphate-containing catalyst compositions described in the art are strontium compounds described in U.S. Pat. No. 4,505,784 as useful for the synthesis of various amines and other nitrogen-containing compounds.

Iron phosphates, usually both stoichiometric and crystalline, are also well known, but have none of the properties required for catalyst or catalyst support applications. For instance, Tsuhako, et al., (Nippon Kagaku Kaishi, No. 2, 1980, pp. 176–180) describe the preparations and properties of eight crystalline iron phosphates all of which are stoichiometric and have PO$_4$/Fe ratios greater than 1.0. Leumann and Lutz, (Galvanotechnik, Vol. 68, No. 8, 1977, pp. 715–719) among others have described the "iron phosphates" which are produced in the treatment of phosphate-containing wastewaters. Such materials are usually stoichiometric FePO$_4$ and, again, are not catalytic materials.

The art has long recognized the utility of the addition of alkylene oxides to acrylic or methacrylic acid, always in the presence of appropriate inhibitors, to produce 2-hydroxyalkyl (meth)acrylates. A catalyst is always required for this addition. Catalysts mentioned in the art include ammonium salts (U.S. Pat. No. 3,059,024), ammonium ion exchange resins (British Patent 1003346), phosphonium salts (German Patents 2527116 and 2527117), and lithium, sodium and potassium salts of the (meth)acrylate anion (Japanese Patent 7251382; French Patent 1556337; and U.S. Pat. No. 3,214,988). A number of transition metal catalysts, as salts, are also known to the art, including copper (U.S. Pat. No. 3,709,928), titanium (Japanese Patent 6902686), vanadium (Japanese Patent 8187537), niobium or ruthenium (U.S. Pat. No. 4,223,160), chromium (U.S. Pat. No. 4,404,395), and iron (U.S. Pat. No. 4,365,081).

Of these catalysts, the iron salts are the ones most frequently taught in the art as catalyzing the production of 2-hydroxyalkyl (meth)acrylates from alkylene oxides and acrylic or methacrylic acid. The chromium salts are second most frequently taught in the art. British Patent 1003346, French Patents 1357422 and 1357423, U.S. Pat. Nos. 3,804,884 and 3,340,295, Belgian Patent 657517, Netherlands Patent 6700738, and Japanese Patent 7017662, all of which teach the use of ion exchange resins as catalysts, teach the use of heterogeneous (that is, insoluble throughout the reaction) catalysts in the production of 2-hydroxyalkyl (meth)acrylates from alkylene oxides and acrylic or methacrylic acid. Most often, the catalyst is soluble in the reactants and the products, and a separation step of the product from the catalyst is required.

This discussion of the prior art is presented to show the various compositions and methods of preparing such compositions which are well known in the existing art, and to show the types of catalysts that are well known in the existing art to promote the formation of 2-hydroxyalkyl (meth)acrylates. These documents are only illustrative of a large body of patents and articles, but the documents cited are believed to reflect the teachings most relevant to this invention.

SUMMARY OF THE INVENTION

The catalysts of this invention comprise non-stoichiometric phosphates of the following formula: $M(PO_4)_yX'$.

Thus, $M_3(PO_4)_1$ is a stoichiometric metal phosphate, while $M^{+3}{}_1(PO_4)_{0.5}$ is a non-stoichiometric metal phosphate. Since the valence requirements of the metal M must be satisfied, these non-stoichiometric compositions contain additional anionic species, $OH^-$ and $O^{2-}$. Such compositions also contain water, either coordinated to the metal and hence an integral part of the structure, or present simply as incidental water of hydration. The catalysts are uniform and amorphous in nature and, specifically, are not simply mixtures of phosphate and oxide and/or hydroxide compounds.

The surface characteristics of the catalysts of the present invention contribute to excellent activity. The pore volume, pore size distribution and surface area necessary to have active catalysts are produced by proper control of key variables in the preparation process. Thus, this invention provides specific process steps and conditions to achieve the desired results.

In general terms and using $Fe^{+3}$ as a focus of discussion, the process for preparing the catalysts can be carried out as follows. First an aqueous ferric solution is prepared from a suitable iron salt. An appropriate phosphate source, e.g., orthophosphoric acid is then added to the ferric solution. The resulting iron/phosphate solution is then mixed with and reacted with a pH-adjusting medium, preferably an alkaline solution such as dilute aqueous ammonia and the like to affect gelation or precipitation of the desired non-stoichiometric metal slurry phosphate composition. Other orders of mixing are also permitted. The pH, concentration, temperature, and mixing time will influence the stoichiometry and structure and hence the utility of the product obtained. The resultant slurry is then generally agitated for a period of time to assure complete reaction. The solid is then separated from the liquid phase by conventional methods such as filtration or centrifugation. Washing and drying may be done by any convenient means. The catalyst may now be formed into the appropriate shape and size. Finally, calcination may be conducted to remove excess water. Forming of the catalyst may, in some cases, be done most conveniently at an earlier stage, such as before washing or between washing and drying.

Catalysts of this invention have particular utility for certain industrially important catalytic processes involving the esterification of unsaturated carboxylic acids, in particular 2-hydroxyalkyl esters of acrylic and methacrylic acids. The catalysts of this invention are heterogeneous catalysts for the production of these esters, and provide an advantage because the separation of the catalyst from the pure product requires only a filtering step. The catalysts are highly active and selective and provide unexpected advantages in the ease of production and the purity of the product.

THE INVENTION

It has been found that certain inorganic non-stoichiometric metal phosphates have special utility as heterogeneous catalysts and comprise compounds of the following formula:

$$M(PO_4)_y X'$$

Where
M is a metal, preferably a transition metal with a +3 valence such as $Fe^{+3}$, $Cr^{+3}$ and the like;
y is the phosphate-to-metal mole ratio, which is in the range of from about 0.1 to 0.6 and preferably from about 0.1 to 0.3, X' represents other anionic species to satisfy the valence requirements of the metal.

The catalysts of this invention are also characterized by their amorphous nature, that is there are no crystalline phases detected when these compositions are examined by conventional x-ray diffraction methods. Further, the catalysts are uniform in nature in that separate phases of, for example, "FePO_4" and $Fe_2O_3$ or $Fe(OH)_3$ are not present. Additionally, the novel catalytic compositions having surface areas and pore volumes greater than 100 m²/g and 0.1 cc/g, respectively, are most preferred.

The catalysts of this invention can be prepared as irregular powders or granules, but most often will be used as regular shapes such as microspherical beads, larger beads, or particles with cylindrical cross sections, as are commonly used in heterogeneous catalysis. While these compositions can be used without dilution or the use of a support, such dilution can be desirable for economic reasons or to enhance the physical properties of the final product. Thus, inert inorganic materials, particularly oxides such as silica, alumina, titania and the like can be physically mixed with the compositions at whatever stage of the preparation is most convenient. The inert "support" may be present at the point of gelation or precipitation. The level of diluent or support when employed may range from 10 to 90% w/w.

The process for preparing the catalysts comprises the following steps:
1. Preparing a dilute aqueous solution of an appropriate metal salt;
2. Preparing a dilute aqueous solution of an appropriate phosphate;
3. Mixing 1 and 2, and, if required, adding pH adjuster;
4. Aging the resultant product slurry;
5. Separating the solid catalyst composition from the slurry;
6. Washing the solid catalyst composition;
7. Drying;
8. Forming the catalyst into the desired size and shape particles; adding an inert diluent if desired; and
9. Calcining, if required,.

Each of these steps will now be considered in detail.

The metal salt may be any water-soluble salt of the metal desired which has the needed valence (oxidation state). Salts of strong acids are particularly suitable. Thus, for example, ferric nitrate, ferric sulfate and ferric chloride are appropriate. In general, +3 oxidation state transition metals produce the preferred catalytic properties—$Fe^{+3}$, $Cr^{+3}$, $Ce^{+3}$, and the like are preferred transition metals. The metal salt solution is usually dilute, having 1 to 10% solids by weight.

The phosphate solution may be prepared separately from the metal salt solution, or may be prepared at the same time if the required $PO_4/M$ mole ratio can be obtained without any reaction between the metal and phosphate. Suitable phosphate sources include orthophosphoric acid, ammonium phosphate, ammonium hydrogen phosphate and ammonium dihydrogen phosphate and the like. This solution is also dilute, having 1 to 10% solids by weight. Mixing of these solutions is accomplished by any convenient means. Both can be added individually to a third pH-adjusting solution, or the combined metal/phosphate solution can be added to the pH-adjusting solution. The mixing must be done efficiently with relatively short mixing times to assure preparation of a homogeneous product.

The pH-adjusting solution is most conveniently dilute aqueous ammonia, but other alkaline materials may be suitable. The final pH of the mixture should be 3 to 11; preferably 7 to 11; and most preferably 8 to 10.

The mixing is usually carried out at ambient temperature, but a temperature as low as 0° C. and as high as 100° C. may enhance the physical properties of the product. Aging for a period of 1 to 24 hours at a temperature from about 25° C. to about 100° C. can also enhance the physical properties of the product. Adjustment of pH or salt content during such aging also can provide improved properties.

Washing can be done by a decant-and-settle method or by washing on a centrifuge or filtration device. Washing is best done with deionized or distilled water.

Drying is generally accomplished by conventional means such as forced hot air, vacuum or spray drying. The temperature should be controlled to avoid decomposition of the catalyst composition. Temperatures less than 200° C. are preferred.

Forming of the catalyst into the sizes and shapes of particles most suited to a particular application can be done by techniques well known in the art. Thus, spray drying, extrusion, pelleting or various spheroidization methods are effective. Inclusion of a diluent can be beneficial. Forming or dilution can be done at various stages of the preparation as dictated by the requirements of the specific forming method chosen. Suitable diluents well known in the art can be used, but silica has been found to be particularly suitable.

Finally, the preparation process can include a calcination step. Such calcination, normally in air but suitably done in other atmospheres such as nitrogen or $H_2O$-containing gases, will improve product strength and reduce the moisture content. Reducing moisture content is important from a catalytic standpoint, since $H_2O$ may participate in unwanted non-selective reactions. Calcination temperatures of 250°–400° C. produce the desired water loss without causing undesired changes in catalyst properties.

The catalysts of this invention can be used as heterogeneous catalysts for the esterification of unsaturated carboxylic acids, especially the 2-hydroxyalkyl esters of acrylic and methacrylic acids, from the acid and the appropriate alkylene oxide. In particular, the catalysts of this invention can be used with great advantage when the alkylene oxide is ethylene oxide or propylene oxide. The catalysts may be used in any suitable reactor and may be used in batch or continuous processes. In a batch process the catalysts should be used at any effective level, usually from about 10 to about 70 wt % iron, preferably from 20 to 50 wt % iron, based on the initial weight of acid charged. In a continuous process the instantaneous catalyst/liquid weight ratio will be in the corresponding range. The reaction temperature is from about 30° to about 90° C., but preferably from about 50° to about 70° C. The reaction is carried out in the presence of suitable polymerization inhibitors that are known in the art. Separation of the catalyst from the product is accomplished by any convenient means such as filtration, decantation, or centrifugation. It is desirable to recycle the catalyst, once separated. Separation of the catalyst from the product is improved over the prior art since the catalyst is essentially insoluble in the product.

The catalysts may be used in any convenient particle size. For a slurry process, particle size may range from a few microns to several millimeters. For fixed bed processes, as are well known in the catalyst art, particle size will normally be 1 to 10 mm. Factors other than reactor design, i.e., fixed bed versus slurry, may also influence the choice of particle size. Examples of such factors are diffusion, pressure drop or filterability, any of which may be important with a particular feed/product/process combination.

The use of the catalysts of this invention provides an advantage over catalysts that are known in the art for the production of 2-hydroxyalkyl esters of acrylic and methacrylic acids. The catalysts of this invention show higher selectivity for the desired product as well as higher activity, with the advantage that the reaction may be run at lower temperatures. While the reaction temperature can vary widely it will be lower than those required by prior art catalysts and will still be complete more quickly than when run in the presence of catalysts that are known in the art. This obviously lowers the energy required and is therefore a more economical process.

EXAMPLES

The following examples illustrate certain embodiments of our invention. These examples are not provided to establish the scope of the invention, which is described in the disclosure and recited in the claims. The proportions are in parts by weight (pbw) or percent by weight (%/wt) unless otherwise indicated.

Example 1

Catalyst Preparation

A solution is prepared by dissolving 690 g ferric sulfate hydrate and 75 g of 85% $H_3PO_4$ in 3000 g of deionized water. That solution is added dropwise to a well-stirred solution of 1468 g of 28% aqueous ammonia in 12,450 g of deionized water. The final solution has a pH of 10. The resultant flocculent brown precipitate is removed by filtration using a conventional vacuum filtration apparatus and washed with copious quantities of deionized water until the pH of the filtrate is about 7. The solid product is removed from the filter, dried in a forced air oven at 105° C. and ground to the desired particle size before evaluation. Analysis shows stoichiometry of this product to be:

$$Fe(PO_4)_{0.2}O_{1.2}(OH)_{1.2}(H_2O)_{1.2} \cdot 0.2H_2O$$

The ground, sized product has a surface area of 261 $m^2/g$ and a pore volume of 0.18 cc/g.

Example 2

Solubility of Catalyst

The product's solubility is evaluated in acrylic acid (AA) and hydroxyethylacrylate (HEA). AA and HEA are examples of the feed and product, respectively, of an esterification process in which the catalyst is useful. At 70° C. no solubility was observed in HEA and at 70° C. a solubility of only about 100 ppm in AA was observed. This low solubility is most desirable for catalysts to be used in heterogeneous esterification processes. Even a relatively soluble catalyst would have only a limited life and would contaminate the product. Stoichiometric iron phosphates and oxides are very soluble in AA, HEA and similar organic acids and esters.

Example 3

Effect of Calcining

The product of Example 1 is calcined in air at 400° C. for two hours. The physical properties of the material are unchanged, but its solubility in AA is further reduced to less than half that previously observed.

To demonstrate the utility of the catalysts of this invention in the production of unsaturated esters, the following examples are presented.

Example 4

Preparation of HEA

A 500 ml Fischer-Porter reactor bottle equipped with a stirring bar is charged with the catalyst from Example 1 (2.8 g). Acrylic acid (2.0 g) is added and the reactor bottle is connected to a multiported reactor head (67% iron). The reactor is pressure tested, then evacuated. Ethylene oxide (4.7 g) is added as a gas at room temperature to a predetermined pressure. Gas addition is halted and the reactor is heated to 50° C. and held at that temperature for 1 hour. The catalyst is stirred in the solution throughout. The reactor is cooled to room temperature and the excess ethylene oxide is vented. A 20-minute nitrogen sparge of the product/catalyst mixture ensures additional removal of unreacted ethylene oxide. The mixture is filtered to remove catalyst and the resulting 2-hydroxyethylacrylate (HEA) is analyzed. The results among those of ensuing examples are presented in Table 1.

TABLE 1

| HEA Analyses from Examples 4, 8, 9, 10, 12 and 13 (wt %) | | | | |
|---|---|---|---|---|
| Example | AA | HEA | EGDA | DEGMA |
| 4 | 2.28 | 85.0 | 0.05 | 4.39 |
| 8 | 1.94 | 89.3 | 0.05 | 5.04 |
| 9 | 2.72 | 84.7 | 0.05 | 5.76 |
| 10 | 1.33 | 90.6 | 0.05 | 5.73 |
| 13 | 3.29 | 78.1 | 0.10 | 7.14 |
| 13 | 33.60 | 39.6 | 0.12 | 6.58 |

AA = Acrylic Acid
HEA = Hydroxyethyl Acrylate
EDGA = Ethyleneglycol Diacrylate
DEGMA = Diethyleneglycol Monoacrylate

Example 5

The procedure of Example 4 is repeated, except with less catalyst (1.9 g, 46% iron), with methacrylic acid (2.0 g) used in place of acrylic acid, and slightly less ethylene oxide added (3.8 g). The reactor is heated to 70° C. for 1 hour. The results for the product hydroxyethylmethacrylate (HEMA) are presented in Table 2.

TABLE 2

| HEMA Analyses from Examples 5 and 11 (area %) | | | | |
|---|---|---|---|---|
| Example | MAA | HEMA | EGDMA | DEGMMA |
| 5 | 2.31 | 76.2 | 1.34 | 3.65 |
| 11 | 3.70 | 86.8 | 0.17 | 3.17 |

MAA = Methacrylic Acid
HEMA = Hydroxyethyl Methacrylate
EGDMA = Ethyleneglycol Dimethacrylate
DEGMMA = Diethyleneglycol Monomethacrylate

Example 6

The procedure of Example 4 is repeated, except propylene oxide (6.7 g) is used in place of ethylene oxide. Since propylene oxide is a volatile liquid at room temperature, it is chilled to ice temperature, then added to the reactor by gas-tight syringe after the evacuation step. The nitrogen sparge time is increased to 1 hour to ensure removal of unreacted propylene oxide from the product solution. The results for the product hydroxypropylacrylate (HPA) are presented in Table 3.

TABLE 3

| HP(M)A Analyses from Examples 6 and 7 (area %) | | | | |
|---|---|---|---|---|
| Example | (M)AA | HP(M)A | PGD(M)A | DPGM(M)A |
| 6 | 6.85 | 60.79 | 0.27 | 1.92 |
| 7 | 4.48 | 91.40 | 0.34 | — |

(M)AA = (Meth)acrylic Acid
HP(M)A = Hydroxypropyl (Meth)acrylate
PGD(M)A = Propyleneglycol Di(meth)acrylate
DPGM(M)A = Dipropyleneglycol Mono(meth)acrylate

Example 7

The procedure of Example 6 is repeated, except methacrylic acid (2.0 g) is used in place of acrylic acid, and the reaction is carried out for 1 hour at 70° C. The results for the product hydroxypropyl (meth)acrylate (HPMA) are presented in Table 3.

Example 8

A 500 ml Fischer-Porter reactor bottle is equipped with a stirring bar and charged with the catalyst from Example 1 (72.9 g). Acrylic acid (100.0 g) and inhibitors are added and the reactor bottle is connected to a multiported reactor head (35% iron). The reactor is pressure tested, evacuated, then filled with 5% oxygen in nitrogen to 10 psig at room temperature. Ethylene oxide (72 g) is added as a liquid at the reaction temperature (50° C.), never exceeding 30 psig in the reactor. The addition of the ethylene oxide occurs over approximately 1 hour, and the reactor remains at temperature another 2 hours. The catalyst is suspended in the stirred solution throughout the experiment. The reactor is vented, and the reactor is sparged with nitrogen for 30 minutes as the reactor is cooled to room temperature. The product is decanted from the catalyst and the resulting 2-hydroxyethylacrylate (HEA) is analyzed. The results presented in Table 1 are similar to those obtained for the smaller scale reaction, example 1 except the yields of HEA is somewhat higher.

Example 9

The procedure of Example 8 is repeated reusing the same catalyst recovered in Example 8. The results presented in Table 1 indicate the catalyst is effective when reused.

Example 10

The procedure of Example 8 repeated reusing, again, the catalyst recovered in Example 9. The results presented in Table 1 suggest that the catalyst when washed with methanol and reused is as effective as a fresh catalyst.

Example 11

The procedure of Example 10 is repeated, except with methacrylic acid (100.0 g) used in place of acrylic acid. The reactor is heated to 70° C. The results for the product hydroxyethylmethacrylate (HEMA) are presented in Table 2.

Example 12

As an example that the catalysts of this invention result in an improvement in product purity over a typical homogeneous catalyst taught in the art for the production of HEA, the procedure of Example 4 is followed with $FeCl_3$ (0.029 g, 0.5% iron) as catalyst. The reactor is heated to 65° C. for 2 hours. The results for the product hydroxyethylacrylate (HEA) presented in Table 1 show that the catalysts of our invention are superior to those of the prior art. The yield of the desired product is higher and produced at a lower temperature and shorter time.

Example 13

As an example that the catalysts of this invention are significantly different from stoichiometric, commercially available iron phosphate, the procedure of Example 4 is followed with $FePO_4$—$H_2O$ (1.9 g, 19.5% iron) as the catalyst for the reaction of acrylic acid (3.0) and ethylene oxide (4.6 g). The reactor was heated to 65° C. for 2 hours. The results for the product hydroxyethylacrylate (HEA) presented in Table 1 indicate the stoichiometric iron phosphate to be an unacceptable material.

Example 14

The process of Example 1 is followed exactly through the precipitation step. The resultant flocculent brown precipitate is then washed using multiple slurry decant steps. After the final decantation the slurry contains about 6% wt/wt of the solid catalyst composition, $Fe_x(PO_4)_yX'$. Then 300 g of this slurry is mixed with 100 g of a commercially available silica and extruded using conventional, well known techniques. The ⅛" diameter extruded catalyst is found to have a surface area of 167 m²/g, a pore volume of 1.2 cc/g, and an average pore radius of 145 Å.

Example 15

A solution is prepared by dissolving 69.0 g ferric sulfate hydrate and 300.0 g 85% orthophosphoric acid in 197 g of deionized water. That solution is added slowly to a well stirred solution of 146 g of 28% aqueous ammonia in 1245 g of deionized water. The final slurry has a pH of 9.8. The resultant flocculent brown precipitate is separated from the mother liquor and washed with copious quantities of deionized water using a conventional vacuum filtration apparatus. The product is dried in a forced air oven. The dried product is found to have a BET surface area of 1.4 m²/g and has a calculated $PO_4/Fe$ ratio of 0.88. This very unsatisfactory low surface area demonstrates that only certain ranges of composition are suitable.

What is claimed is:

1. A non-stoichiometric, amorphous catalyst for the esterification of unsaturated carboxylic acids of the formula:

$$Fe(PO_4)_y X'$$

wherein y is from 0.2 to 0.6 and X' represents other anionic species to satisfy the valence requirement of the iron.

* * * * *